US008591450B2

(12) United States Patent
DeFonzo

(10) Patent No.: US 8,591,450 B2
(45) Date of Patent: Nov. 26, 2013

(54) DIALYSIS CATHETER

(75) Inventor: Stephan A. DeFonzo, Wayne, PA (US)

(73) Assignee: Rex Medical L.P., Conshohocken, PA (US)

( * ) Notice: Subject to any disclaimer, the term of this patent is extended or adjusted under 35 U.S.C. 154(b) by 3 days.

(21) Appl. No.: 13/108,154

(22) Filed: May 16, 2011

(65) Prior Publication Data

US 2011/0301522 A1 Dec. 8, 2011

Related U.S. Application Data

(60) Provisional application No. 61/352,195, filed on Jun. 7, 2010.

(51) Int. Cl.
*A61M 37/00* (2006.01)
*A61M 1/00* (2006.01)
*A61M 3/00* (2006.01)
*A61M 25/00* (2006.01)

(52) U.S. Cl.
USPC ............... 604/6.16; 604/28; 604/43; 604/523

(58) Field of Classification Search
USPC .......................................... 604/6.16, 28, 433
See application file for complete search history.

(56) References Cited

U.S. PATENT DOCUMENTS

| | | | |
|---|---|---|---|
| 1,248,492 A | 12/1917 | Hill | |
| 2,024,982 A | 12/1935 | Scott | |
| 2,460,473 A | 2/1949 | Larkin et al. | |
| 3,336,927 A | 8/1967 | Klebanoff | |
| 3,411,534 A | 11/1968 | Rose | |
| 3,680,562 A | 8/1972 | Wittes et al. | |
| 3,815,608 A | 6/1974 | Spinosa et al. | |
| 3,833,003 A | 9/1974 | Taricco | |
| 3,929,126 A | 12/1975 | Corsaut | |
| 3,938,530 A | 2/1976 | Santomieri | |
| 3,963,028 A | 6/1976 | Cooley et al. | |

(Continued)

FOREIGN PATENT DOCUMENTS

| | | |
|---|---|---|
| DE | 2590645 | 5/1987 |
| EP | 0301854 | 2/1989 |

(Continued)

OTHER PUBLICATIONS

Moureau, Modified Seldinger Insertion Technique for PICC Insertion: The New Wave for Nurses.

(Continued)

*Primary Examiner* — Jacqueline Stephens
*Assistant Examiner* — Andrew J Mensh
(74) *Attorney, Agent, or Firm* — Neil D. Gershon

(57) ABSTRACT

A dialysis catheter including a first portion having an outer wall having a first diameter, an elongated distal portion having a second diameter smaller than the first diameter, and a transition region between the first portion and distal portion. A first longitudinally extending venous lumen is configured to deliver blood. First and second independent longitudinally extending arterial lumens are configured to withdraw blood from a patient. The venous lumen and arterial lumen have first and second regions each positioned a first distance from the outer wall of the catheter and a third region positioned a second shorter distance from the outer wall of the catheter to form an arch shaped wall portion progressively increasing in thickness from the third region toward the first region and from the third region to the second region.

7 Claims, 8 Drawing Sheets

(56) References Cited

U.S. PATENT DOCUMENTS

| | | | |
|---|---|---|---|
| 4,129,129 | A | 12/1978 | Amrine |
| 4,134,402 | A | 1/1979 | Mahurkar |
| 4,178,936 | A | 12/1979 | Newcomb |
| 4,180,068 | A | 12/1979 | Jacobsen et al. |
| 4,270,535 | A | 6/1981 | Bogue et al. |
| 4,299,228 | A | 11/1981 | Peters |
| D264,246 | S | 5/1982 | Ekbladh et al. |
| 4,345,602 | A | 8/1982 | Yoshimura |
| D270,282 | S | 8/1983 | Gross |
| 4,398,910 | A | 8/1983 | Blake et al. |
| 4,403,983 | A | 9/1983 | Edelman et al. |
| 4,406,656 | A | 9/1983 | Hattler et al. |
| 4,431,426 | A | 2/1984 | Groshong et al. |
| 4,432,752 | A | 2/1984 | Marlon |
| 4,439,179 | A | 3/1984 | Lueders et al. |
| 4,451,252 | A | 5/1984 | Martin |
| 4,453,928 | A | 6/1984 | Steiger |
| D275,519 | S | 9/1984 | Ismail |
| 4,479,792 | A | 10/1984 | Lazarus et al. |
| 4,490,136 | A | 12/1984 | Ekbladh et al. |
| 4,493,696 | A | 1/1985 | Uldall |
| 4,511,163 | A | 4/1985 | Harris et al. |
| 4,543,087 | A | 9/1985 | Sommercorn et al. |
| 4,545,373 | A | 10/1985 | Christoudias |
| 4,548,597 | A | 10/1985 | Nelson |
| 4,568,329 | A | 2/1986 | Mahurkar |
| 4,574,806 | A | 3/1986 | McCarthy |
| 4,581,012 | A | 4/1986 | Brown et al. |
| 4,583,968 | A | 4/1986 | Mahurkar |
| 4,610,670 | A | 9/1986 | Spencer |
| 4,619,643 | A | 10/1986 | Bai |
| 4,623,327 | A | 11/1986 | Mahurkar |
| 4,639,252 | A | 1/1987 | Kelly et al. |
| D288,361 | S | 2/1987 | Lichtman |
| 4,643,711 | A | 2/1987 | Bates |
| 4,668,221 | A | 5/1987 | Luther |
| 4,670,009 | A | 6/1987 | Bullock |
| 4,682,978 | A | 7/1987 | Martin |
| 4,692,141 | A | 9/1987 | Mahurkar |
| 4,717,379 | A | 1/1988 | Ekholmer |
| 4,738,667 | A | 4/1988 | Galloway |
| 4,753,640 | A | 6/1988 | Nichols et al. |
| 4,762,120 | A | 8/1988 | Hussein |
| 4,769,016 | A | 9/1988 | Labianca |
| 4,776,841 | A | 10/1988 | Catalano |
| 4,808,155 | A | 2/1989 | Mahurkar |
| 4,808,163 | A | 2/1989 | Laub |
| 4,832,687 | A | 5/1989 | Smith |
| 4,838,881 | A | 6/1989 | Bennett |
| 4,842,582 | A | 6/1989 | Mahurkar |
| 4,846,804 | A | 7/1989 | Davis et al. |
| 4,894,057 | A | 1/1990 | Howes |
| 4,895,561 | A | 1/1990 | Mahurkar |
| 4,902,276 | A | 2/1990 | Zakko |
| 4,904,238 | A | 2/1990 | Williams |
| 4,927,418 | A | 5/1990 | Dake et al. |
| 4,950,259 | A | 8/1990 | Geary et al. |
| 4,961,809 | A | 10/1990 | Martin |
| 4,968,307 | A | 11/1990 | Dake et al. |
| 4,976,684 | A | 12/1990 | Broadnax, Jr. |
| 4,994,027 | A | 2/1991 | Farrell |
| 4,995,865 | A | 2/1991 | Gahara et al. |
| 5,009,636 | A | 4/1991 | Wortley et al. |
| 5,017,192 | A | 5/1991 | Dodge et al. |
| 5,021,044 | A | 6/1991 | Sharkawy |
| D318,123 | S | 7/1991 | Yokoyama et al. |
| 5,041,084 | A | 8/1991 | DeVries et al. |
| 5,053,004 | A | 10/1991 | Markel et al. |
| 5,053,023 | A | 10/1991 | Martin |
| 5,057,073 | A | 10/1991 | Martin |
| 5,057,075 | A | 10/1991 | Moncrief et al. |
| 5,059,170 | A | 10/1991 | Cameron |
| 5,078,699 | A | 1/1992 | Haber et al. |
| 5,092,848 | A | 3/1992 | deCiutiis |
| 5,098,413 | A | 3/1992 | Trudell et al. |
| 5,122,125 | A | 6/1992 | Deuss |
| 5,135,599 | A | 8/1992 | Martin et al. |
| 5,139,486 | A | 8/1992 | Moss |
| 5,154,704 | A | 10/1992 | Archibald |
| 5,156,592 | A | 10/1992 | Martin et al. |
| 5,167,623 | A | 12/1992 | Cianci et al. |
| 5,171,216 | A | 12/1992 | Dasse et al. |
| 5,174,477 | A | 12/1992 | Schafer |
| 5,203,056 | A | 4/1993 | Funk et al. |
| 5,207,648 | A | 5/1993 | Gross |
| 5,207,650 | A | 5/1993 | Martin |
| 5,209,723 | A | 5/1993 | Twardowski et al. |
| 5,209,742 | A | 5/1993 | Venema et al. |
| 5,213,111 | A | 5/1993 | Cook |
| 5,215,527 | A | 6/1993 | Beck et al. |
| 5,221,255 | A | 6/1993 | Mahurkar et al. |
| 5,221,256 | A | 6/1993 | Mahurkar et al. |
| 5,234,438 | A | 8/1993 | Semrad |
| 5,238,218 | A | 8/1993 | Mackal |
| 5,246,430 | A | 9/1993 | MacFarlane |
| 5,250,038 | A | 10/1993 | Melker et al. |
| 5,270,003 | A | 12/1993 | Bernes et al. |
| 5,273,527 | A | 12/1993 | Schatz et al. |
| 5,279,596 | A | 1/1994 | Castaneda et al. |
| 5,318,515 | A | 6/1994 | Wilk |
| 5,318,546 | A | 6/1994 | Bierman |
| 5,320,599 | A | 6/1994 | Griep et al. |
| 5,324,274 | A | 6/1994 | Martin |
| 5,334,139 | A | 8/1994 | Jeppsson |
| 5,338,293 | A | 8/1994 | Jeppsson et al. |
| 5,346,471 | A | 9/1994 | Raulerson |
| 5,348,536 | A | 9/1994 | Young et al. |
| 5,350,358 | A | 9/1994 | Martin |
| 5,360,397 | A | 11/1994 | Pinchuk |
| 5,364,344 | A | 11/1994 | Beattie et al. |
| 5,374,245 | A | 12/1994 | Mahurkar |
| 5,378,230 | A | 1/1995 | Mahurkar |
| 5,380,276 | A | 1/1995 | Miller et al. |
| 5,380,290 | A | 1/1995 | Makower et al. |
| 5,382,238 | A | 1/1995 | Abrahamson et al. |
| 5,395,316 | A | 3/1995 | Martin |
| 5,401,256 | A | 3/1995 | Stone et al. |
| 5,403,291 | A | 4/1995 | Abrahamson |
| 5,405,341 | A | 4/1995 | Martin |
| 5,431,661 | A | 7/1995 | Koch |
| 5,451,206 | A | 9/1995 | Young |
| 5,453,098 | A | 9/1995 | Botts et al. |
| 5,468,159 | A | 11/1995 | Brodsky et al. |
| 5,486,159 | A | 1/1996 | Mahurkar |
| 5,489,278 | A | 2/1996 | Abrahamson |
| 5,509,897 | A | 4/1996 | Twardowski et al. |
| 5,509,900 | A | 4/1996 | Kirkman |
| 5,542,925 | A | 8/1996 | Orth |
| 5,556,390 | A | 9/1996 | Hicks |
| 5,569,182 | A | 10/1996 | Twardowski et al. |
| 5,571,093 | A | 11/1996 | Cruz et al. |
| 5,593,392 | A | 1/1997 | Starchevich |
| 5,662,144 | A | 9/1997 | Lo et al. |
| 5,662,606 | A | 9/1997 | Cimino et al. |
| 5,693,030 | A | 12/1997 | Lee et al. |
| 5,702,365 | A | 12/1997 | King |
| 5,707,362 | A | 1/1998 | Yoon |
| 5,713,849 | A | 2/1998 | Bosma et al. |
| 5,718,678 | A | 2/1998 | Fleming, III |
| 5,728,115 | A | 3/1998 | Westcott et al. |
| 5,752,939 | A | 5/1998 | Makoto |
| 5,792,123 | A | 8/1998 | Ensminger |
| 5,807,311 | A | 9/1998 | Palestrant |
| 5,807,317 | A | 9/1998 | Krech |
| 5,807,329 | A | 9/1998 | Gelman |
| 5,810,789 | A | 9/1998 | Powers et al. |
| 5,817,116 | A | 10/1998 | Takahashi et al. |
| 5,827,229 | A | 10/1998 | Auth |
| 5,830,196 | A | 11/1998 | Hicks |
| 5,852,347 | A | 12/1998 | Marcotte |
| 5,865,813 | A | 2/1999 | DeKalb et al. |
| 5,911,715 | A | 6/1999 | Berg et al. |
| 5,916,208 | A | 6/1999 | Luther et al. |
| 5,919,160 | A | 7/1999 | Sanfilippo |

(56) References Cited

U.S. PATENT DOCUMENTS

| | | | |
|---|---|---|---|
| 5,931,829 A | 8/1999 | Burbank | |
| 5,944,732 A | 8/1999 | Raulerson et al. | |
| 5,961,485 A | 10/1999 | Martin | |
| 5,961,486 A | 10/1999 | Twardowski et al. | |
| 5,976,103 A | 11/1999 | Martin | |
| 5,976,120 A | 11/1999 | Chow et al. | |
| 5,984,908 A | 11/1999 | Davis et al. | |
| 5,989,213 A * | 11/1999 | Maginot | 604/28 |
| 6,001,079 A | 12/1999 | Pourchez | |
| 6,010,480 A | 1/2000 | Abele et al. | |
| 6,036,654 A | 3/2000 | Quinn et al. | |
| 6,059,771 A | 5/2000 | Balbierz et al. | |
| D427,307 S | 6/2000 | Guala et al. | |
| 6,089,527 A | 7/2000 | Utterberg | |
| 6,106,540 A | 8/2000 | White et al. | |
| 6,110,185 A | 8/2000 | Barra et al. | |
| 6,113,062 A | 9/2000 | Schnell et al. | |
| 6,120,494 A | 9/2000 | Jonkman | |
| D431,650 S | 10/2000 | Guala et al. | |
| 6,132,405 A | 10/2000 | Nilsson et al. | |
| 6,146,354 A * | 11/2000 | Beil | 604/28 |
| 6,146,373 A | 11/2000 | Cragg et al. | |
| 6,152,909 A | 11/2000 | Bagaoisan et al. | |
| 6,156,016 A | 12/2000 | Maginot | |
| 6,161,812 A | 12/2000 | Guala et al. | |
| 6,180,059 B1 | 1/2001 | Divino, Jr. et al. | |
| 6,190,349 B1 | 2/2001 | Ash et al. | |
| 6,190,371 B1 | 2/2001 | Maginot et al. | |
| 6,193,685 B1 | 2/2001 | Goodin | |
| 6,196,519 B1 | 3/2001 | Utterberg | |
| 6,196,996 B1 | 3/2001 | Teirstein | |
| 6,206,849 B1 | 3/2001 | Martin et al. | |
| 6,210,365 B1 | 4/2001 | Afzal | |
| 6,210,370 B1 | 4/2001 | Chi-Sing et al. | |
| 6,223,070 B1 | 4/2001 | Chait | |
| 6,234,448 B1 | 5/2001 | Porat | |
| 6,264,627 B1 | 7/2001 | Liska et al. | |
| 6,270,490 B1 | 8/2001 | Hahnen | |
| 6,273,879 B1 | 8/2001 | Keith et al. | |
| 6,293,927 B1 | 9/2001 | McGuckin, Jr. | |
| 6,293,958 B1 | 9/2001 | Berry et al. | |
| 6,296,631 B2 | 10/2001 | Chow | |
| 6,328,730 B1 | 12/2001 | Harkrider, Jr. | |
| 6,346,093 B1 | 2/2002 | Allman et al. | |
| 6,350,252 B2 | 2/2002 | Ray et al. | |
| 6,358,229 B1 | 3/2002 | Tihon | |
| 6,361,529 B1 | 3/2002 | Goodin et al. | |
| 6,394,141 B2 | 5/2002 | Wages et al. | |
| 6,454,742 B1 | 9/2002 | Noecker et al. | |
| 6,454,997 B1 | 9/2002 | Divino, Jr. et al. | |
| 6,544,270 B1 | 4/2003 | Zhang | |
| D474,269 S | 5/2003 | Choksi et al. | |
| 6,592,558 B2 | 7/2003 | Quah | |
| 6,595,966 B2 | 7/2003 | Davey et al. | |
| 6,620,118 B1 | 9/2003 | Prosl | |
| 6,644,618 B1 | 11/2003 | Balbo | |
| 6,666,853 B2 | 12/2003 | Chu et al. | |
| 6,682,044 B2 | 1/2004 | Miller | |
| 6,692,466 B1 | 2/2004 | Chow et al. | |
| 6,699,184 B2 | 3/2004 | Felix et al. | |
| 6,701,648 B2 | 3/2004 | Battaglia | |
| 6,749,574 B2 | 6/2004 | O'Keefe | |
| 6,758,836 B2 | 7/2004 | Zawacki | |
| 6,758,857 B2 | 7/2004 | Cioanta et al. | |
| 6,770,057 B2 | 8/2004 | Feliciano | |
| 6,780,175 B1 | 8/2004 | Sachdeva et al. | |
| 6,786,884 B1 | 9/2004 | DeCant, Jr. et al. | |
| 6,814,718 B2 | 11/2004 | McGuckin, Jr. et al. | |
| 6,821,265 B1 | 11/2004 | Bertolero et al. | |
| 6,823,617 B2 | 11/2004 | Schweikert | |
| 6,827,710 B1 | 12/2004 | Mooney et al. | |
| 6,858,019 B2 | 2/2005 | McGuckin, Jr. et al. | |
| 6,890,321 B2 | 5/2005 | Luther et al. | |
| 6,911,014 B2 | 6/2005 | Wentling et al. | |
| 6,921,396 B1 | 7/2005 | Wilson et al. | |
| 6,923,793 B2 | 8/2005 | Ishida et al. | |
| 6,942,635 B2 | 9/2005 | Rosenblatt et al. | |
| 6,942,647 B2 | 9/2005 | Nickels | |
| 6,969,095 B2 | 11/2005 | Rittenhouse | |
| 6,969,381 B2 | 11/2005 | Voorhees | |
| 6,974,434 B2 | 12/2005 | Roberts et al. | |
| 6,979,323 B2 | 12/2005 | Rogers et al. | |
| 6,986,752 B2 | 1/2006 | McGuckin, Jr. | |
| 6,994,700 B2 | 2/2006 | Elkins et al. | |
| 6,997,900 B2 | 2/2006 | Weststrate | |
| 7,008,395 B1 | 3/2006 | Loggie | |
| 7,008,412 B2 | 3/2006 | Maginot | |
| 7,011,645 B2 | 3/2006 | McGuckin, Jr. et al. | |
| 7,060,060 B1 | 6/2006 | Simpson et al. | |
| 7,077,829 B2 | 7/2006 | McGuckin, Jr. et al. | |
| 7,128,734 B1 | 10/2006 | Wilson et al. | |
| 7,276,043 B2 | 10/2007 | Heath | |
| 7,300,430 B2 * | 11/2007 | Wilson et al. | 604/523 |
| 7,322,953 B2 | 1/2008 | Redinger | |
| 7,393,339 B2 | 7/2008 | Zawacki | |
| 7,556,612 B2 | 7/2009 | Voorhees | |
| 7,569,029 B2 | 8/2009 | Clark | |
| 7,615,034 B2 | 11/2009 | DiFiore | |
| 7,645,273 B2 | 1/2010 | Lualdi | |
| 7,731,708 B2 | 6/2010 | Haarala | |
| 7,799,015 B2 | 9/2010 | Schweikert | |
| 7,833,157 B2 | 11/2010 | Gottlieb | |
| 7,833,214 B2 | 11/2010 | Wilson | |
| 7,871,398 B2 | 1/2011 | Chesnin | |
| 7,879,021 B2 | 2/2011 | Drewes | |
| 2002/0055714 A1 | 5/2002 | Rothschild | |
| 2002/0087145 A1 | 7/2002 | Ehwald et al. | |
| 2003/0023198 A1 | 1/2003 | Twardowski | |
| 2003/0066218 A1 | 4/2003 | Schweikert | |
| 2003/0088213 A1 | 5/2003 | Schweikert et al. | |
| 2003/0093027 A1 | 5/2003 | McGuckin, Jr. et al. | |
| 2003/0153898 A1 | 8/2003 | Schon et al. | |
| 2003/0204179 A1 | 10/2003 | Davey et al. | |
| 2003/0225365 A1 | 12/2003 | Greff et al. | |
| 2004/0064086 A1 | 4/2004 | Gottlieb et al. | |
| 2004/0193103 A1 | 9/2004 | Kumar | |
| 2004/0249337 A1 | 12/2004 | DiFiore | |
| 2005/0187535 A1 | 8/2005 | Wilson et al. | |
| 2006/0004325 A1 | 1/2006 | Hamatake et al. | |
| 2006/0047268 A1 | 3/2006 | Stephens | |
| 2006/0135949 A1 | 6/2006 | Rome et al. | |
| 2006/0206048 A1 | 9/2006 | Loggie | |
| 2007/0149919 A1 | 6/2007 | Perkins et al. | |
| 2008/0097409 A1 | 4/2008 | Stephens | |
| 2008/0154186 A1 | 6/2008 | Appling et al. | |
| 2008/0214980 A1 | 9/2008 | Anand | |
| 2008/0287919 A1 | 11/2008 | Kimball | |
| 2008/0306427 A1 | 12/2008 | Bailey | |
| 2008/0312578 A1 * | 12/2008 | DeFonzo et al. | 604/6.16 |
| 2009/0024078 A1 | 1/2009 | Abe | |
| 2009/0088699 A1 | 4/2009 | King | |
| 2009/0099550 A1 | 4/2009 | Carrillo | |
| 2009/0118661 A1 | 5/2009 | Moehle | |
| 2009/0157052 A1 | 6/2009 | Verbitsky | |
| 2009/0204052 A1 | 8/2009 | Nimkar | |
| 2009/0216174 A1 | 8/2009 | Nardeo | |
| 2009/0221950 A1 | 9/2009 | Atkins | |
| 2010/0057020 A1 | 3/2010 | Uretsky | |
| 2010/0081986 A1 | 4/2010 | Matson | |
| 2010/0100074 A1 | 4/2010 | Smith | |
| 2010/0145285 A1 | 6/2010 | Bosel | |
| 2010/0168642 A1 | 7/2010 | Appling | |
| 2010/0168718 A1 | 7/2010 | Bellisario | |
| 2010/0191165 A1 | 7/2010 | Appling | |
| 2010/0210990 A1 | 8/2010 | Lyons | |

FOREIGN PATENT DOCUMENTS

| | | |
|---|---|---|
| EP | 0440992 | 8/1991 |
| EP | 0691139 | 1/1996 |
| EP | 0799627 | 10/1997 |
| EP | 0995461 | 4/2000 |

(56) References Cited

FOREIGN PATENT DOCUMENTS

| EP | 1905476 | 4/2008 |
| WO | WO-9737699 | 10/1997 |
| WO | WO-9824501 | 6/1998 |
| WO | WO-0074760 | 12/2000 |
| WO | WO-0176677 | 10/2001 |
| WO | WO-2004/036102 | 4/2004 |

OTHER PUBLICATIONS

Seldinger Technique for Introducing Catheters.
Journal of Vascular and Interventional Radiology 12:376-378 (2001), "Sheathless Technique of Ash Split-Cath Insetion", Aalpen Patel, MD; Stephen Hofkin, MD; David Ball, DO; Gary Cohen, MD and Douglas C. Smith, MD.
Eyal Barzel, "An Implantable Dialysis Catheter", Mar. 1998.

* cited by examiner

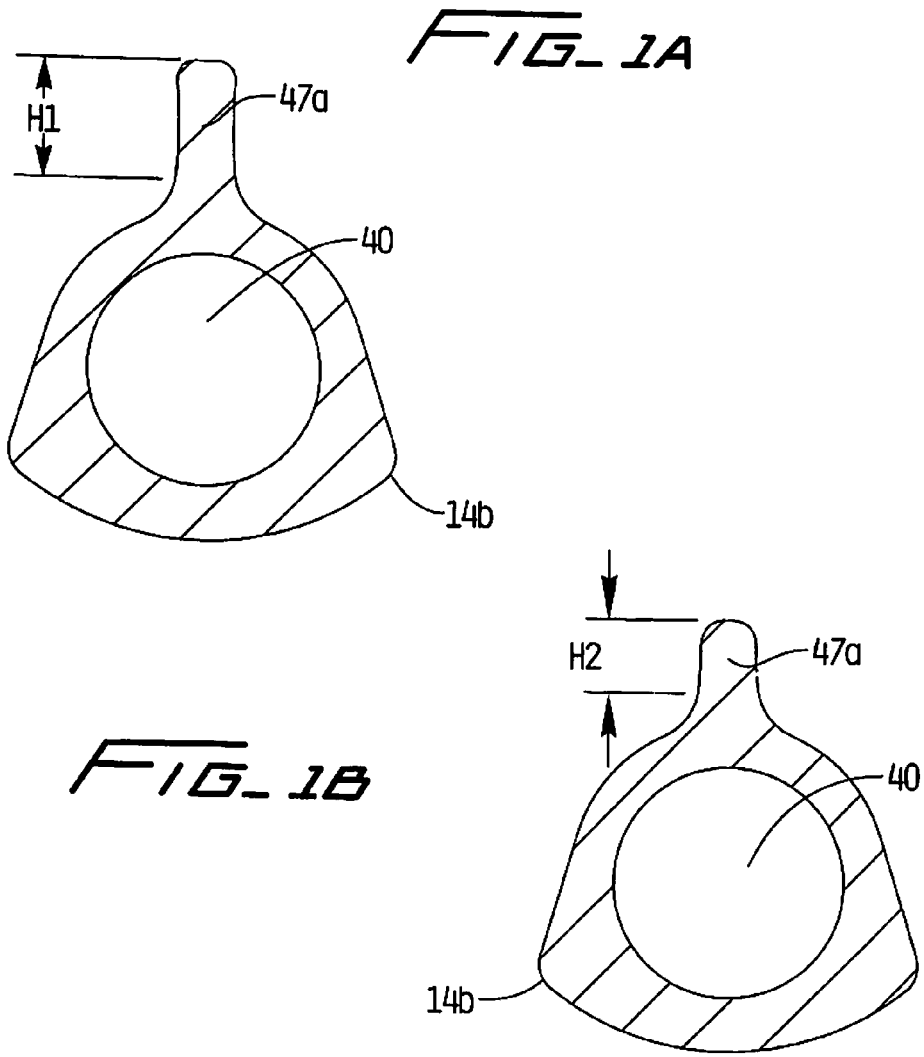

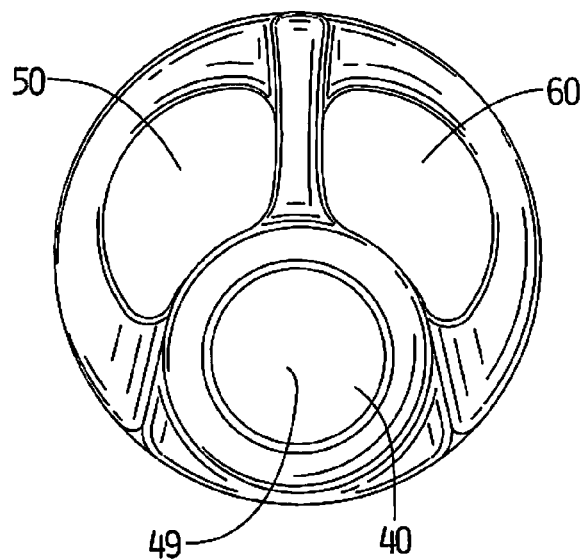
FIG_2
FIG_4
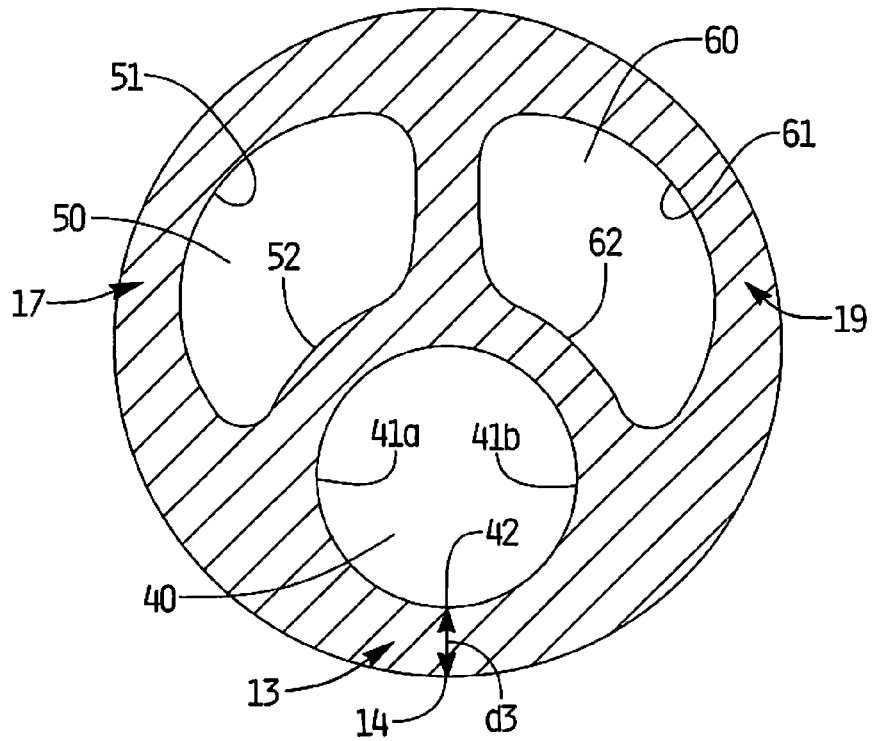

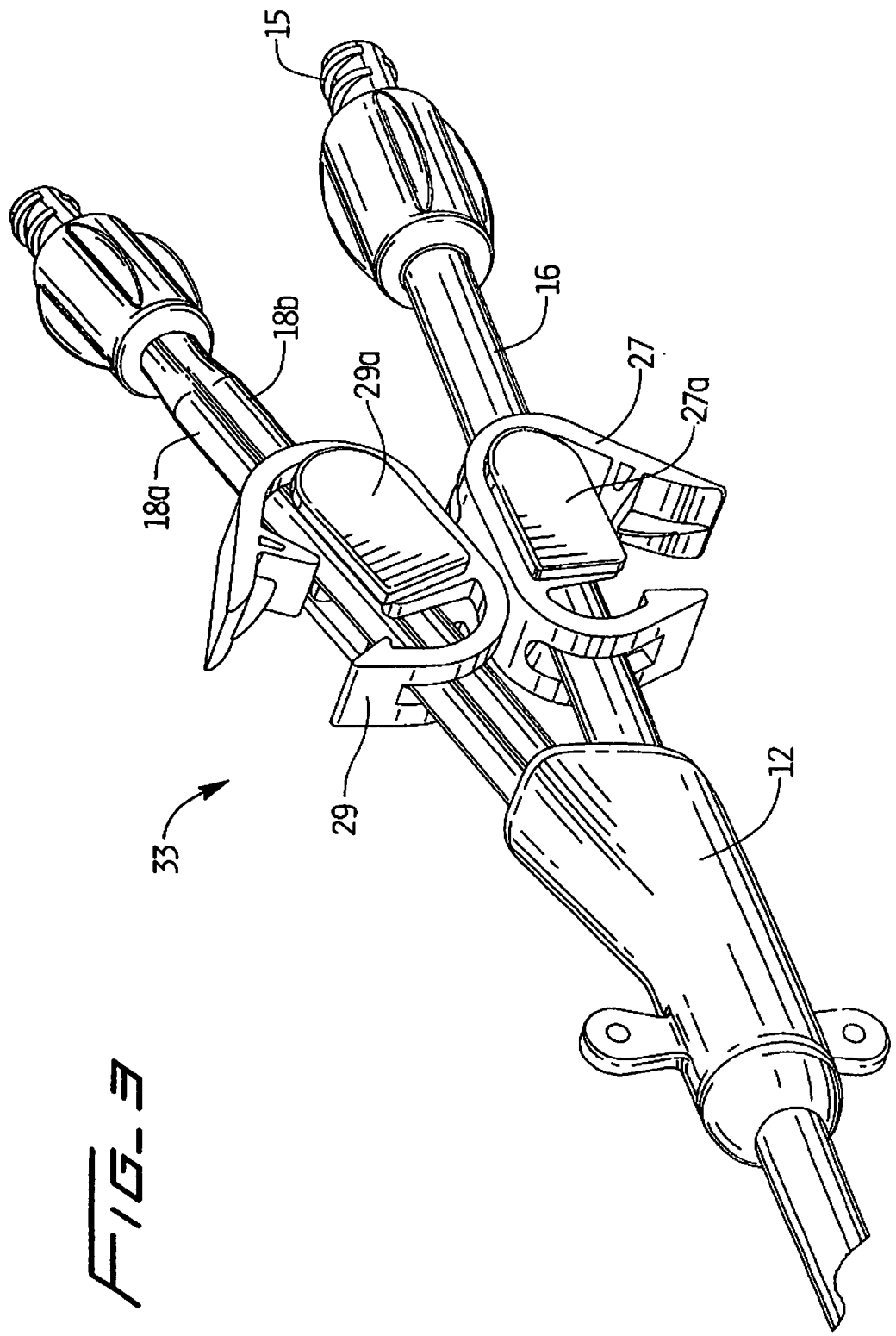

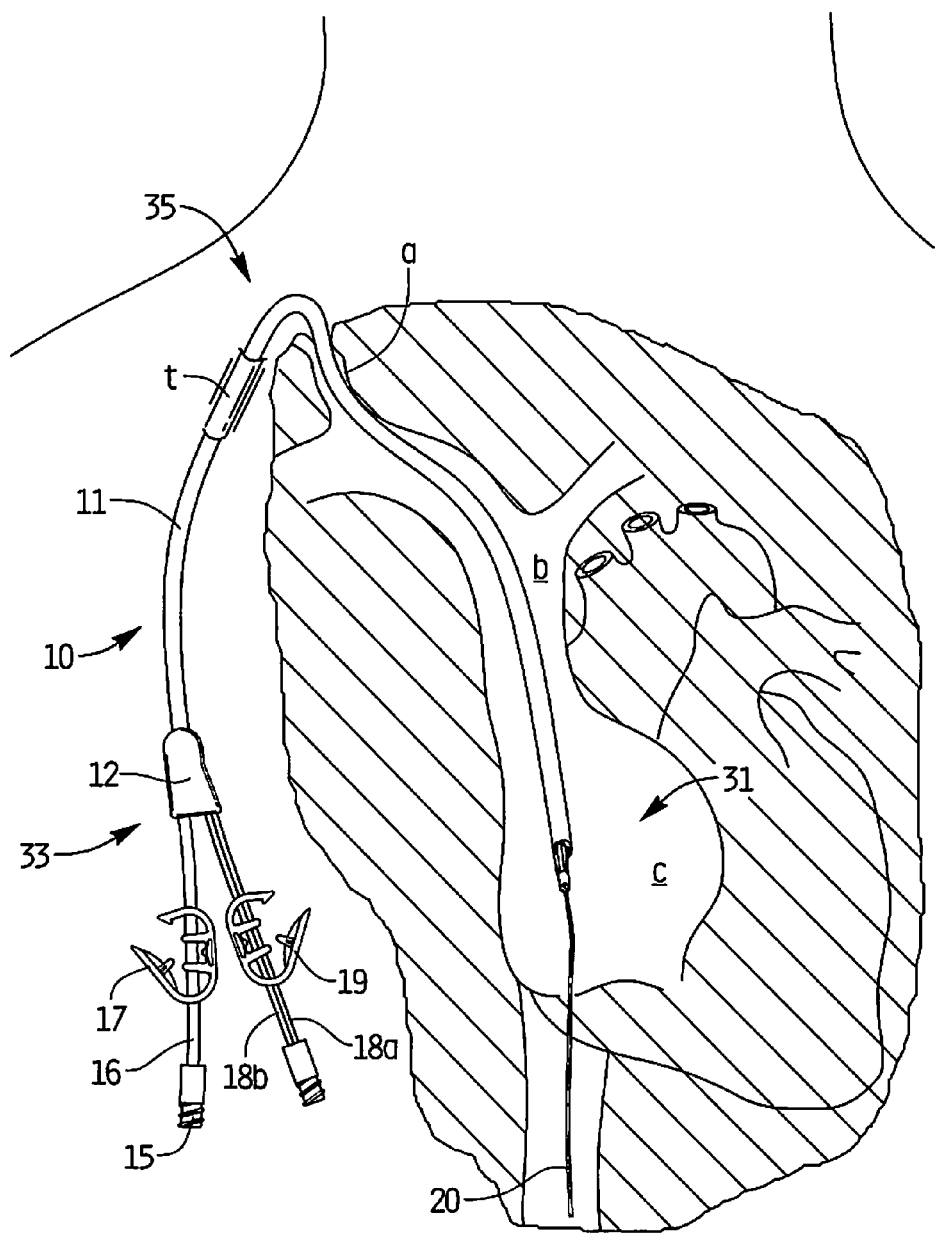

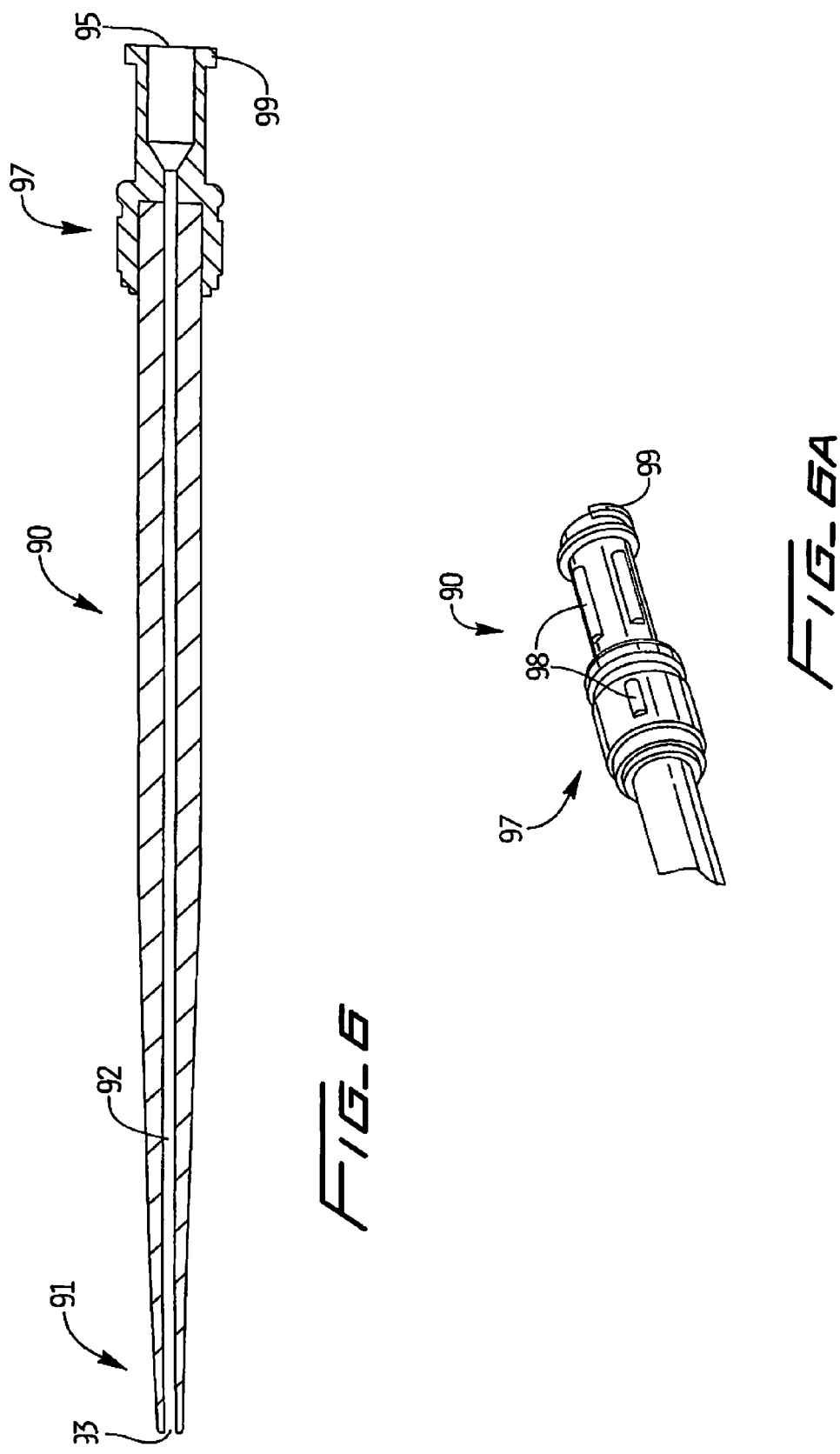

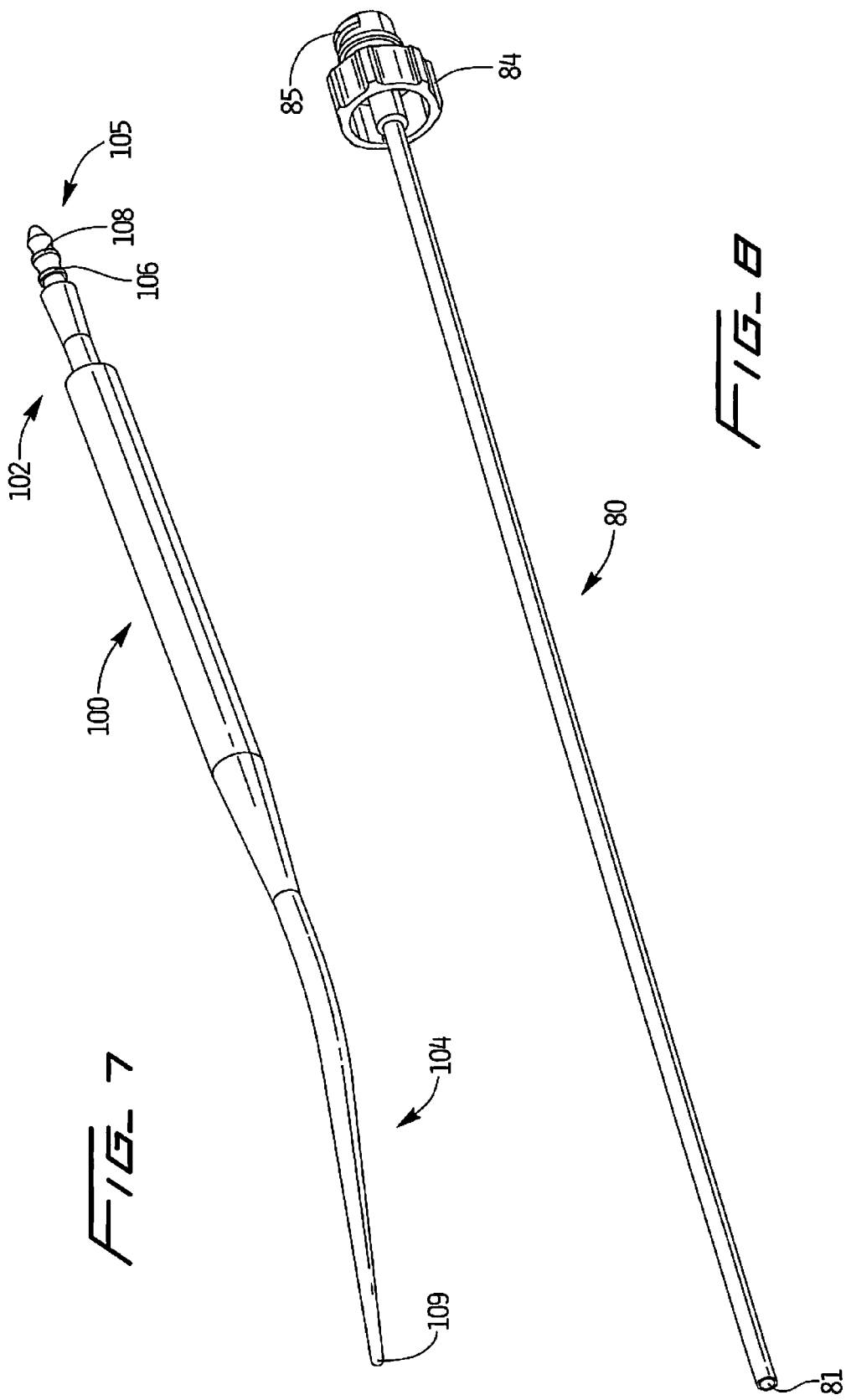

DIALYSIS CATHETER

BACKGROUND

This application claims priority from provisional application 61/352,195, filed Jun. 7, 2010, the entire contents of which are incorporated herein by reference.

TECHNICAL FIELD

This application relates to a catheter and more particularly to a multi-lumen catheter which facilitates hemodialysis.

BACKGROUND OF RELATED ART

Hemodialysis is a well known method of providing renal (kidney) function by circulating blood. The kidneys are organs which function to extract water and urea, mineral salts, toxins, and other waste products from the blood with filtering units called nephrons. From the nephrons the collected waste is sent to the bladder for excretion. For patients having one or both defective kidneys, the hemodialysis procedure is life saving because it provides a machine to simulate the function of the kidneys.

In the hemodialysis procedure, blood is withdrawn from the patient's body through a catheter or tube and transported to a dialysis machine, also commonly referred to as a kidney machine. The catheter is typically inserted through the jugular vein and maneuvered into position through the superior vena cava into the right atrium to provide high blood flow. In the dialysis machine, toxins and other waste products diffuse through a semi-permeable membrane into a dialysis fluid closely matching the chemical composition of the blood. The filtered blood, i.e. with the waste products removed, is then returned to the patient's body. In some instances, the catheter may be left in place for several years. As can be appreciated, proper access to the patient's blood and transport of the blood to and from the dialysis machine for this extended period of time is critical to hemodialysis.

One example of a dialysis catheter currently being marketed is the MedComp Ash Split catheter. This catheter has two lumens, one for arterial flow and the other for venous flow, which are each D-shaped in cross-sectional configuration. The catheter is bifurcated at its distal end to separate the lumens and the catheter is manually split to the desired length for selected separation before insertion into the target area. Another well-known catheter is a Med Comp catheter which has the venous flow lumen terminating proximally, i.e. axially recessed, from the arterial flow lumen. Each of these lumens is also D-shaped in cross-sectional configuration.

The use of a tear away sheath in catheter insertion is well known. It would be advantageous if a dialysis catheter could be provided which would also provide for readily insertion without the use of a tear away sheath in certain instances. Such insertion method, if utilized, can decrease the complexity of the procedure.

Another area of dialysis catheter design is to maximize venous and arterial flow rates while preventing collapsing the lumens. That is, it is known that the larger lumens will maximize flow rates, reduce arterial and venous pressure and improve dialysis by providing fastener dialysis. However, given the limited amount of space in the dialysis catheter, which is typically about 15-16 French, the size of the lumens is limited. The size is also limited by the fact that if the lumens are too large, the wall thickness of the catheter becomes too thin, thereby reducing the strength of the wall and resulting in collapse of the lumens which has a detrimental affect on the blood flow.

In navigating vessels to access the target site, such as the right atrium, it is desirable to provide the smallest catheter profile, i.e. the smallest outer diameter catheter body. This profile facilitates insertion through smaller vessels as it reduces the likelihood of the catheter engaging the wall of the vessel and reduces trauma to the vessel by minimizing frictional contact with the vessel wall. However, the desire for smaller diameter catheters must be balanced against the need for providing sufficient sized lumens to enable proper blood flow. If the lumens are too small, sufficient blood flow may not be able to be maintained and the blood can be damaged during transport. Also, a sufficient relationship must be maintained between the size of the lumens and the overall diameter of the catheter to maintain the structural integrity of the catheter.

Numerous attempts have been made in the prior art to optimize the multi-lumen configuration. In some approaches, such as disclosed in U.S. Pat. Nos. 4,568,329 and 5,053,023, the inflow and outflow lumen are provided side by side in D-shaped form. In other approaches, such as those disclosed in U.S. Pat. Nos. 4,493,696, 5,167,623 and 5,380,276 the inflow and outflow tubes are placed in concentric relation. Other examples of different lumen configurations are disclosed in U.S. Pat. Nos. 5,221,256, 5,364,344, and 5,451,206. Commonly assigned U.S. Pat. Nos. 6,814,718 and 7,011,645 disclose other lumen configurations.

The catheter lumen configuration must accommodate two competing factors: keeping the catheter as small as possible to facilitate insertion while keeping the lumens as large as possible for blood flow. This balance must be achieved while maintaining the structural integrity of the catheter. It would therefore be advantageous to provide a catheter which reaches an optimum compromise between these two competing factors.

Another important feature of dialysis catheters is the suction openings to withdraw blood. Keeping the suction openings clear of thrombolytic material and away from the vessel wall is clearly essential to dialysis function since an adequate supply of blood must be removed from the patient to be dialyzed.

The need therefore exists for an improved dialysis catheter which facilitates the surgical dialysis procedure, reduces unwanted kinking of the catheter during insertion and use, and strikes an optimal balance between overall catheter size and lumen size.

SUMMARY

The present invention provides in one aspect a dialysis catheter comprising an outer wall, a first portion having a first diameter, an elongated distal portion having a second diameter smaller than the first diameter, and a transition region between the first portion and distal portion. A first longitudinally extending substantially circular venous lumen configured to deliver blood is positioned off center of a central longitudinal axis of the catheter and terminates in a distal opening at the distalmost end of the catheter.

The catheter includes first and second independent longitudinally extending arterial lumens configured to withdraw blood from a patient, each terminating in an opening in the transition region spaced proximally of the distal opening of the venous lumen. The venous lumen is in a venous lumen region and has a first region, a second region and a third region between the first and second regions. The first and second regions are each positioned a first distance from the outer wall of the catheter and the third region is positioned a second distance from the outer wall of the catheter, the second distance being less than the first distance to form a first arch shaped wall portion progressively increasing in thickness from the third region toward the first region and from the third region toward the second region.

The first arterial lumen is in a first arterial lumen region and has a first region, a second region and a third region between the first and second regions. The first and second regions of the first arterial lumen are each positioned a third distance from the outer wall of the catheter, and the third region of the first arterial lumen is positioned a fourth shorter distance from the outer wall of the catheter to form a second arch shaped wall portion progressively increasing in thickness from the third region of the first arterial lumen toward the first region of the first arterial lumen and from the third region of the first arterial lumen toward the second region of the first arterial lumen.

In some embodiments, the transition region tapers toward the distal portion. In some embodiments, a reinforcing rib extends longitudinally from the transition region and terminates proximally of the distalmost end of the catheter.

In some embodiments, the second arterial lumen has a first region, a second region and a third region between first and second regions. The first and second regions of the second arterial lumen are each positioned a fifth distance from the outer wall of the catheter, and the third region of the second arterial lumen is positioned a sixth shorter distance from the outer wall of the catheter to form a third arch shaped wall portion progressively increasing in thickness from the third region of the second arterial lumen toward the first region of the second arterial lumen and from the third region of the second arterial lumen toward the second region of the second arterial lumen. In some embodiments, the third and fifth distances and/or the fourth and sixth distances are substantially equal.

A stiffening member can be removably positionable within the catheter to temporarily increase the stiffness of the catheter to facilitate insertion. The stiffening member can be removably received in the venous lumen and can have a lumen formed therein configured to receive a guidewire therethrough. The stiffening member can extend distally of a distalmost end of the catheter body when inserted therein. The stiffening member can be secured to the catheter by a threaded engagement.

In another aspect, the present invention provides a dialysis catheter comprising an outer wall, a first portion having a first diameter, an elongated distal portion having a second diameter smaller than the first diameter, and a transition region between the first portion and distal portion. A first venous lumen region has a first longitudinally extending substantially circular venous lumen configured to deliver blood, terminating in a distal opening at the distalmost end of the catheter. First and second independent longitudinally extending arterial lumens are configured to withdraw blood from a patient, each of the arterial lumens terminating in an opening in the transition region spaced proximally of the distal opening. The first arterial lumen has a first region, a second region and a third region between the first and second regions. The first and second regions are each positioned a first distance from the outer wall of the catheter, and the third region is positioned a second distance from the outer wall of the catheter, wherein the second distance is less than the first distance to form an arch shaped wall portion in a first arterial lumen region progressively increasing in thickness from the third region toward the first region and from the third region toward the second region of the first arterial lumen.

The second arterial lumen has a first region, a second region and a third region between first and second regions. The first and second regions of the second arterial lumen are each positioned a third distance from the outer wall of the catheter, and the third region of the second arterial lumen is positioned a fourth shorter distance from the outer wall of the catheter to form an arch shaped wall portion in a second arterial lumen region progressively increasing in thickness from the third region of the second arterial lumen toward the first region of the second arterial lumen and from the third region of the second arterial lumen toward the second region of the second arterial lumen.

The venous lumen can be positioned off center of a longitudinal axis of the catheter.

A stiffening member can be removably positionable within the venous lumen of the catheter to temporarily increase stiffness of the catheter to facilitate insertion. The stiffening member can have a lumen dimensioned to receive a guidewire.

In another aspect, the present invention provides a dialysis catheter for delivering and withdrawing blood from a patient's body comprising a catheter body defining four quadrants in a transverse cross-section at an intermediate portion and having first and second arterial lumens and a venous lumen having a substantially circular cross section. The venous lumen is positioned in a portion of the third and fourth quadrants with a first region adjacent the intersection of the four quadrants and a second region opposite the first region. A wall thickness of the catheter at the second region of the venous lumen has a first dimension and increases in thickness in a direction toward the third quadrant and in a direction toward the fourth quadrant to form a first arch shaped wall portion, the arch shaped wall portion thereby having a thinner portion at the portion aligned with a diameter bisecting the first and fourth quadrants from the second and third quadrants and progressively thicker portions in the third and fourth quadrants.

The first arterial lumen is positioned in a portion of the second and third quadrants and the second arterial lumen is positioned in a portion of the first and fourth quadrants, wherein a major portion of the first arterial lumen and the center of the first arterial lumen are positioned in the second quadrant and a major portion of the second arterial lumen and the center of the second arterial lumen are positioned in the first quadrant. The catheter wall portion forms a second arch shaped wall portion adjacent the first arterial lumen having a first pinnacle and first and second portions of increasing thickness extending away from the pinnacle. The first pinnacle preferably lies in the second quadrant.

Preferably, the catheter wall portion forms a third arch shaped wall portion adjacent the second arterial lumen having a second pinnacle and first and second portions of increasing thickness extending away from the second pinnacle. Preferably, the second pinnacle of third arch shaped wall portion lies in the first quadrant.

A stiffening member can be provided removably positionable within the catheter to temporarily increase stiffness of the catheter to facilitate insertion.

BRIEF DESCRIPTION OF THE DRAWINGS

Preferred embodiment(s) of the present disclosure are described herein with reference to the drawings wherein:

FIG. 1A is transverse a cross-sectional view of the catheter taken along line A-A of FIG. 1;

FIG. 1B is a transverse cross-sectional view of the catheter taken along line B-B of FIG. 1;

FIG. 1C is a transverse cross-sectional view of the catheter taken along line C-C of FIG. 1;

FIG. 2 is a front view of the catheter of FIG. 1;

FIG. 3 is a perspective view of a proximal portion of the catheter;

FIG. 4 is a transverse cross-sectional view taken along line 4-4 of FIG. 1;

FIG. 5 is a plan view illustrating insertion of the catheter through the right internal jugular vein and superior vena cava into the right atrium of a patient's body;

FIG. 6 is a longitudinal cross-sectional view of a dilator for use with the insertion of the catheter of FIG. 1;

FIG. 6A is a perspective view of the proximal portion of the dilator of FIG. 6;

FIG. 7 is a perspective view of a tunneling trocar attachable to the catheter of FIG. 1 to aid insertion of the catheter; and FIG. 8 is a perspective view of a stiffener for use with the catheter of FIG. 1 to aid insertion.

DETAILED DESCRIPTION OF PREFERRED EMBODIMENTS

Figure 1:
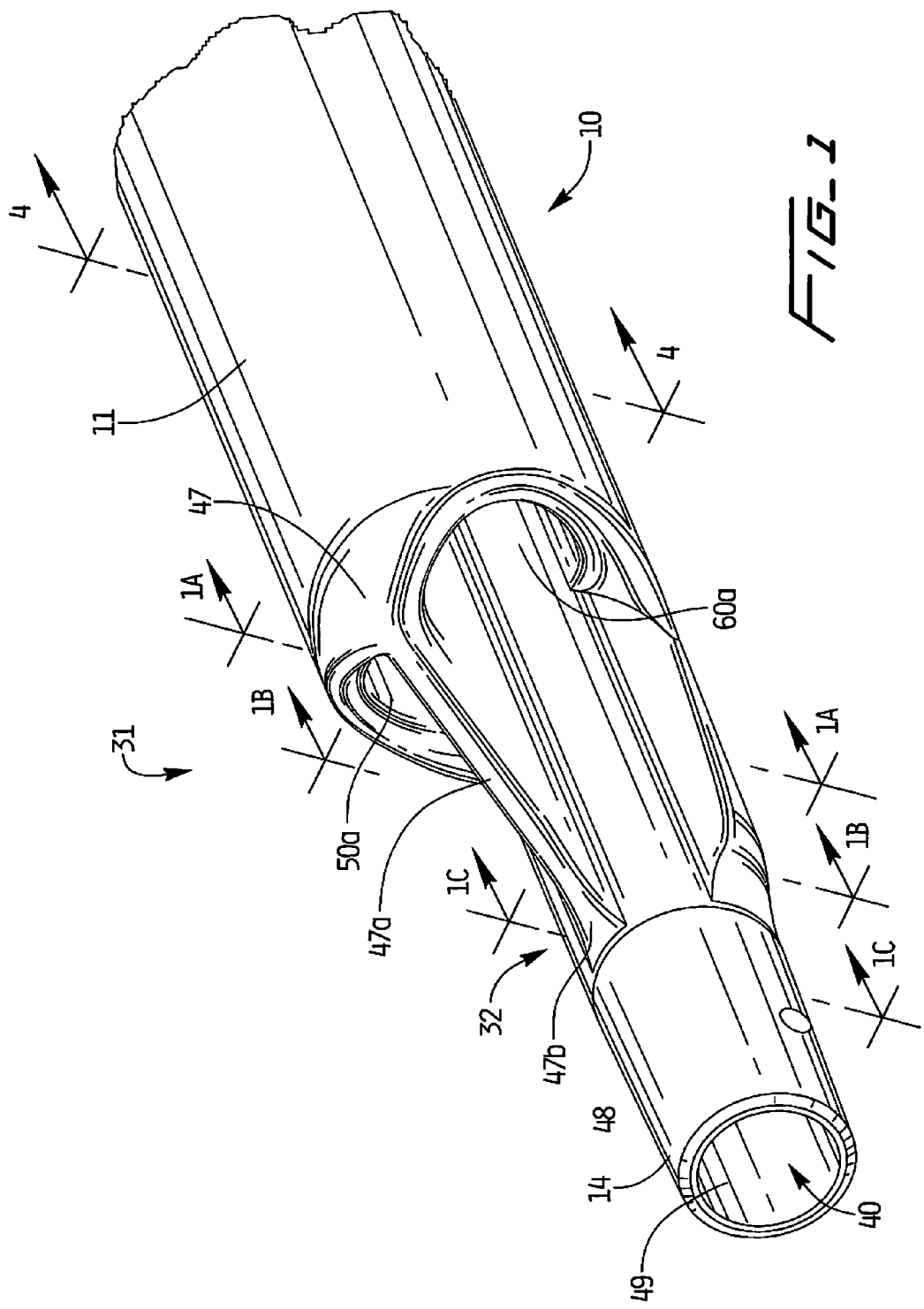
FIG. 1 is a perspective view of the distal portion of the multi-lumen catheter of the present invention.

Referring now in detail to the drawings where like reference numerals identify similar or like components throughout the several views, the catheter of the present invention is designated generally by reference numeral 10. The catheter 10 is typically inserted into an area of high velocity blood flow to ensure sufficient blood can be transported from the body for dialysis. FIG. 5 illustrates the catheter 10 inserted through the right internal jugular vein "a", into the superior vena cava "b", and into the right atrium "c". The catheter 10 can also be inserted for example into the left internal jugular vein, into the superior vena cava "b" and into the right atrium "c". Insertion into the right atrium, from either the right or left side provides the necessary high blood flow to the dialysis machine. Note that the catheter body (catheter tube) 11 is sufficiently flexible to enable it to bend to accommodate the anatomical curves as shown.

With reference to FIGS. 1, 3 and 5, catheter 10 has a catheter body or catheter tube 11 having a distal portion 31 and a proximal portion 33. Distal portion 31 terminates in elongated nose portion 32. Proximal end portion 33 includes hub 12, where the lumens formed within catheter tube 11 are connected, i.e. transition, to the respective inflow and outflow tubes 16 and 18a, 18b, respectively, to enable return and withdrawal of blood for dialysis. Tube clamps 27 and 29 cut off blood flow through inflow and outflow tubes 16, 18a, 18b as desired. As used herein, the terms "inflow" and "outflow" refer to the direction of blood or fluid flow with respect to the catheter such that "return","delivery" or "venous flow" refers to flow from the dialysis machine and delivered to the body while "intake", "withdrawal" or "arterial flow" refers to blood or fluids withdrawn from the body and transported to the dialysis machine.

As shown in FIG. 5, intermediate portion 35 of catheter 10 in certain uses of the catheter extends through subcutaneous tissue tunnel "t", and curves downwardly toward the target site, e.g. the right atrium. This tunnel "t" secures the catheter in place for dialysis for a period of weeks, or even months, with a fibrous cuff enabling tissue ingrowth. The formation of the tunnel "t" and the insertion of the catheter 10 therethrough will be discussed below in conjunction with the discussion of the catheter insertion method.

It should be appreciated that although the catheter is shown emerging from the tissue tunnel "t" at a second incision site, alternatively, the tissue tunnel would not have an exit opening at a second site but instead would exit through the same incision through which initial access is made by the needle and dilator into the internal jugular vein "a". This is described in more detail below.

Several lumens are formed in catheter tube 11 for transporting blood from the patient's body to a dialysis machine. As is well known in the art, a dialysis machine essentially functions as a kidney for patients suffering from kidney failure. Blood is removed from the patient and transported to the dialysis machine where toxins are removed by diffusion through a semi-permeable membrane into a dialysis fluid. The filtered blood is then returned through the lumen of the catheter body to the patient.

Figure 4A:
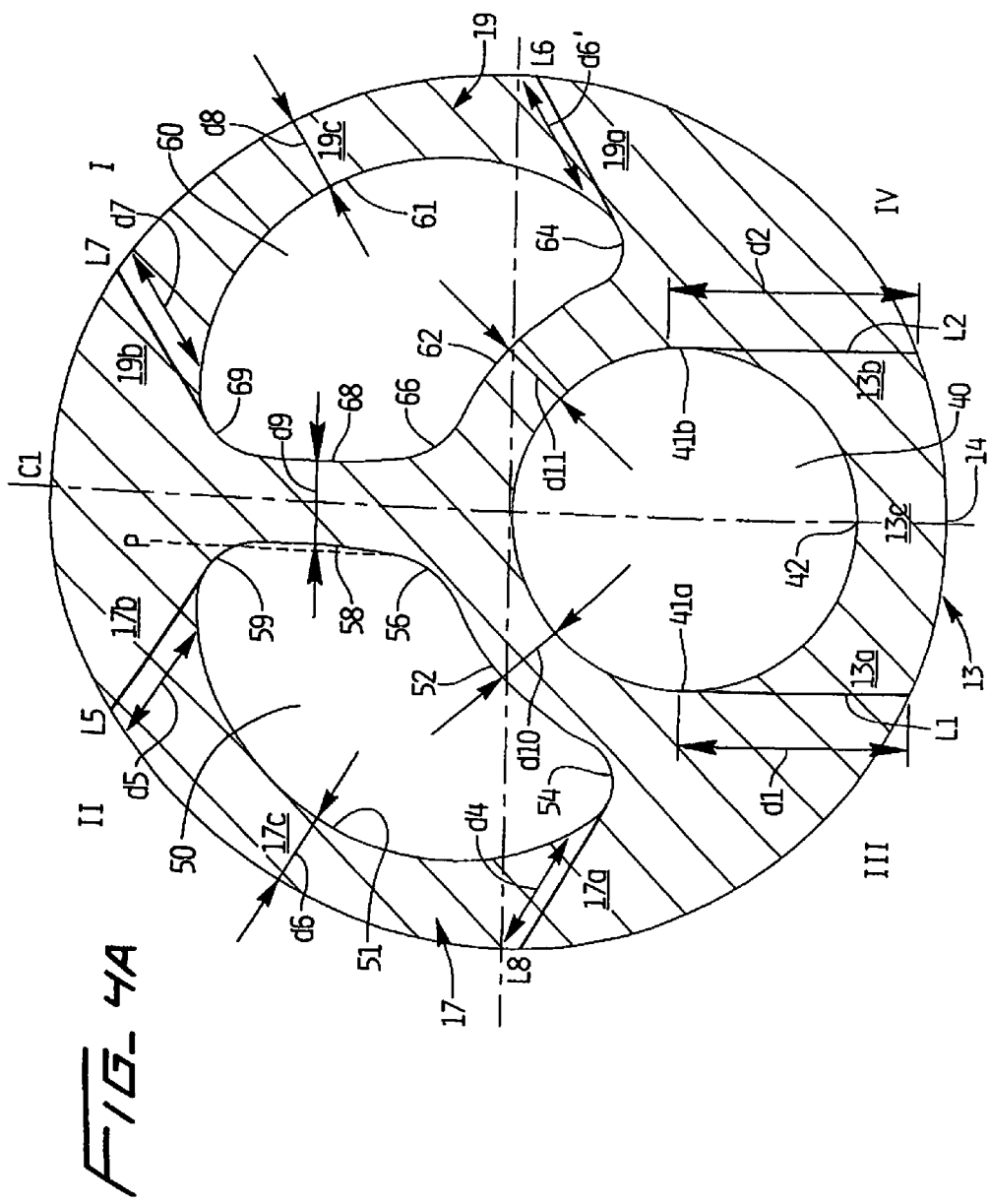
FIG. 4A is an enlarged view similar to FIG. 4 showing the thicknesses of the catheter wall portions and the quadrants of the circle for ease of explanation.

More specifically, and with reference to FIGS. 1, 2 and 4, details of the catheter lumens will now be described. Longitudinally extending venous lumen 40 is formed within catheter tube 11, extends the entire length of the tube and is designed to transport filtered blood to the patient. Lumen 40 extends through the reduced diameter nose portion 32 and is preferably substantially circular in cross section and offset from the central longitudinal axis of the tube 11. As shown in FIG. 4A, a first (or top region as viewed in the orientation of FIG. 4A) lies at the intersection of the four quadrants of the circular cross-section of the catheter tube (or at the center) and the opposite second region lies adjacent the intersection of the third and fourth quadrants. Lumen 40 terminates in distal opening 49 to communicate with the patient's body so blood can be delivered through distal opening 49. One or more side holes 48 can be provided in the side wall of the tube 11 for blood delivery. The lumen 40 preferably has a diameter of about 0.082 inches and a cross-sectional area of about 0.00528 inches.

Venous lumen 40 is also configured to receive a guidewire 20 (FIG. 5) to direct the catheter to the desired position. The guidewire 20 can be received directly through the lumen 40 or if a stiffening member is utilized, the stiffening member would be inserted through the lumen 40 and the guidewire would be inserted through a lumen of the stiffening member (thereby extending through lumen 40).

The wall of the tube forming the venous lumen 40 advantageously forms a bridge or arch to add to the stability of the catheter and limit kinking of the catheter 10 during insertion and use. More specifically, venous lumen region has wall portion 13 having a thicker area 13a and 13b (see FIG. 4A), thereby forming an arch with pinnacle at area 13c. In other words, the thinner portion 13c can be viewed as adjacent the intersection of the third and fourth quadrants, aligned with a diameter dividing the first and fourth quadrants from the second and third quadrants. Thus, the arch increases in thickness as it extends in opposite directions from area 13c into the third and fourth quadrants (containing respective areas 13a, 13b).

In an exemplary embodiment, wherein the diameter of the tube (proximal of the nose portion 32) is about 0.114 inches (tapering to about 0.104 inches) and the diameter of the venous lumen is about 0.082 inches, the distance d1, d2 from the edges 41a, 41b of the lumen 40 to the tube outer wall 14 (see tangent lines L1 and L2) is about 0.054 inches. This can be compared to the distance d3 (FIG. 4) of about 0.021 inches taken from the outer wall tube 14 to the edge 42 of lumen 40 closest to the outer tube wall 14. Thus, the wall thickness (distances from the lumen outer wall to the catheter outer wall) progressively increases in both directions from the d3 designation.

Nose 32, as noted above, can also include side venous (delivery) openings 48 formed through the outer wall 14 wall in fluid communication with lumen 40, also functioning to return blood to the patient's body. Side openings or ports can be angled outwardly if desired to facilitate delivery of blood in the direction of blood flow and lessen mechanical hemolysis. These additional openings help maintain the desired flow volume by distributing the blood through multiple holes. In a preferred embodiment, two openings are provided spaced 120° apart (i.e. each spaced 60 degrees from a bottom wall as viewed in the orientation of FIG. 1 of the catheter 10. It is also contemplated that additional or fewer openings can be provided and the openings can be axially displaced with respect to each other. The openings can be equidistantly spaced about the circumference of the outer wall 14 or asymmetrically spaced. Additional set(s) of openings can also be provided spaced proximally or distally from side openings 48. The nose 32 at the catheter distal portion is elongated and has a diameter less than the diameter of the intermediate portion 35 of catheter 10. By way of example, in one embodiment, the outer diameter of the distal nose portion 32 can be about 0.114 inches and the outer diameter of the intermediate portion 35 can be about 0.208 inches. Clearly other dimensions are contemplated.

The transition portion 47 provides a smooth transition between the intermediate portion 35 and the distal portion 31 as it tapers in a distal direction. Formed in the transition portion 47 (FIG. 1) are two widened open areas 50a, 60a of arterial lumens 50, 60, respectively, separated by a reinforcing rib 47a extending longitudinally. Thus, the intake (arterial) openings terminate in longitudinally aligned openings at the transition portion 47. As shown, the rib 47a, formed during the manufacturing step, extends from the transition region 47 longitudinally and along the reduced diameter nose section 42 to increase rigidity of the catheter. Rib 47a angles toward and into the outer wall 14 of the catheter 10, terminating proximally of venous lumen opening 49. The distal end 47b of the rib 47a can be radiused as it extends longitudinally before blending into the catheter wall 14.

The changing configuration of the catheter 10 at the transition portion 47 can be appreciated by comparing FIGS. 1A-1C which show transverse cross-sectional views along the transition area. As shown, the wall edges 14b transition to a rounder shape in FIG. 1B as they transition to a circular wall of FIG. 1C. Also, the height of the rib 47A decreases in a distal direction (compare height H2 to height H1).

With reference to FIGS. 1, 4 and 4A, catheter 10 also has a pair of independent arterial (withdrawal) lumens 50 and 60 extending longitudinally along the length of the catheter body 11, each terminating at open areas 50a, 60a in transition region 47 so that their opening is proximal to the opening 49 of venous lumen 40. As shown in FIGS. 4 and 4A, lumens 50 and 60 each have an outer curved wall 51, 61 along the side closest to the outer side (wall) of the tube 11. The wall of the tube 11 forming the arterial lumen 50 and arterial lumen 60 advantageously forms a bridge or arch to add to stability of the catheter and limit kinking of the catheter 10 during insertion and use.

More specifically, wall portion 17 of a first arterial lumen region of the catheter has a thicker area 17a and 17b, thereby forming an arch with pinnacle 17c. In an exemplary embodiment, wherein the diameter of the tube (proximal of the nose portion 32) is about 0.114 inches and the diameter of the venous lumen is about 0.082 inches, the distances d4 and d5 from the edge of the lumen 50 to the tube outer wall (see tangent lines L4, L5) is between about 0.041 inches to about 0.042 inches. This can be compared to the distance d6 of about 0.018 inches taken from the outer wall 14 to the edge of the lumen 50 closest to the outer wall 14. Thus, the wall thickness progressively increases in both directions from the d6 designation.

Lumen 60 is similarly dimensioned to lumen 50, with catheter wall portion 19 of second arterial lumen region having a thicker area 19a and 19b, thereby forming an arch with pinnacle 19c. In an exemplary embodiment, wherein the diameter of the tube (proximal of the nose portion 32) is about 0.114 inches and the diameter of the venous lumen is about 0.082 inches, the distance d6', d7 from the edge of the lumen 60 to the tube outer wall (see tangent lines L6, L7) is between about 0.041 inches to about 0.042 inches. This can be compared to the distance d8 of about 0.018 inches taken from outer wall 14 to the edge of the lumen 60 closest to the outer tube wall. Thus, the wall thickness progressively increases in both directions from the d8 designation.

Note, in a preferred embodiment, distances d4, d5, d6' and d7 are substantially equal and distances d6 and d8 are substantially equal.

The shortest distance d9 between the two arterial lumens is preferably about 0.022 inches. Due to the radiused sides, the distance can progressively increase in both directions away from d9 to about 0.024 inches. The distance d10 and d11 between the respective arterial lumens 50, 60 and the venous lumen 40 is preferably about 0.016 inches. Note that the arterial lumen 50 lies in the second and third quadrants, with the center of the lumen 50 and a major portion of the lumen 50 lying in the second quadrant. Note that the arterial lumen 60 lies in the first and fourth quadrants, with the center of the lumen 60 and a major portion of the lumen 60 lying in the first quadrant. Thus, the pinnacle of the arch adjacent the arterial lumen 50 lies in the second quadrant and the pinnacle of the arch adjacent the arterial lumen 60 lies in the first quadrant.

As can be appreciated, the various dimensions provided herein are provided by way of example, it being understood that other dimensions are also contemplated to achieve the arch support to achieve the balance of maximized blood flow with sufficient wall thickness to limit catheter kinking. That is, the lumen configurations are uniquely designed to achieve maximum flow rates through the catheter for enabling procedures such as dialysis while ensuring the catheter is resistant to kinking since kinking will adversely affect blood flow and could reduce the long term effectiveness of the catheter which is designed for long term use. The lumens are also uniquely designed to provide smooth edges so as to prevent blood clotting which could occur with sharper edges. The arches of the catheter wall achieve this. Also, the shape of the venous lumen and the shape of the arterial lumens achieve this. As discussed above, the venous lumen is preferably substantially circular in configuration. Each of the arterial lumens is asymmetrically configured.

More specifically, arterial lumen 50 includes a curved outer wall 51 adjacent the edge closest to the catheter wall 14. Somewhat opposite curved wall 51 is curved or concave inner wall 52. Walls 51 and 52 are joined in quadrant III by a radiused wall 54. A wall 58 with a slight radius with respect to a line (see phantom line P) parallel to a diameter C1 of the catheter dividing the first and fourth quadrants from the second and third quadrants, connects to inner wall 52 via radiused wall 56. Radiused wall 58 transitions into a larger radius wall 59 to join with outer wall 51. Thus, this asymmetrical arterial lumen 50 has radiused walls along all of its sides. The arterial lumen 50 can also be considered somewhat "liver shaped."

Lumen 60 is the mirror image of lumen 50 and thus faces in the opposite direction. Thus, lumen 60 includes a curved outer wall 61 adjacent the edge closest to the catheter wall 14. Somewhat opposite curved wall 61 is curved or concave inner wall 62. Walls 61 and 62 are joined in quadrant IV by a radiused wall 64. A wall 68 with a slight radius with respect to line P connects to inner wall 62 via radiused wall 66. Radiused wall 68 transitions into a larger radius wall 69 to join with outer wall 61. Thus, this asymmetrical arterial lumen 60 has radiused walls along all of its sides. The arterial lumen 60 can also be considered somewhat "liver shaped."

By way of example, walls 59 and 69 can have a radius of curvature of about 0.005 inches to about 0.030 inches, and preferably about 0.013 inches. Walls 58 and 68 can have a radius of curvature of about 0.050 inches to about 0.250 inches, and preferably about 0.150 or about 0.144 inches. The radius of curvature of outer walls 51 and 61 can be about 0.070 inches to about 0.050 inches, and preferably about 0.060 inches. The radius of curvature of walls 56 and 66 can be about 0.005 inches to about 0.030 inches, and preferably about 0.018 inches. Inner radiused walls 52 and 62 can have a radius of curvature of about 0.090 inches to about 0.130 inches, and preferably about 0.114 inches. Walls 54 and 64 can have a radius of curvature of about 0.005 inches to about 0.030 inches, and preferably about 0.010 inches. As can be appreciated, other dimensions are also contemplated.

Although lumens 50 and 60 are isolated along the length of the catheter, they have a common flow source flowing into the separate inflow tubes of catheter 10 via hub 12.

As noted above, in the illustrated embodiment, the venous (return) lumen size preferably ranges from about 0.005 inches to about 0.006 inches$^2$ in cross-sectional area, and is more preferably about 0.00528 inches$^2$. The cross-sectional area of each of the arterial (intake) lumens 50, 60 preferably ranges from about 0.0040 inches to about 0.0048 inches$^2$, and more preferably about 0.00473 inches$^2$, bringing the total cross-sectional area of the intake lumens to about 0.0080 inches to about 0.0096 inches$^2$, and more preferably about 0.00946 inches$^2$. This means that the ratio of total cross sectional area of the return lumen to the intake lumens is preferably about 0.56 to about 1.0. It should be appreciated that other dimensions are also contemplated.

To facilitate insertion, the catheter 10 is configured to receive a stiffening member such as a stiffening member 80 shown in FIG. 8. Stiffing member 80 has a lumen 81 extending therethrough to receive a guidewire, e.g. guidewire 20. Stiffening member (or rod) 80 is inserted into circular venous lumen 40 of catheter 10 to stiffen the flexible catheter for ease in over the wire insertion and navigation through the small vessels. That is, the catheter 10 with stiffener 80 attached thereto and extending through venous lumen 40 is threaded over guidewire 20 (guidewire 20 can be backloaded through the distal opening of lumen 81 of stiffening member 80). The stiffening member 80 can have an internal thread on knob 84 at the proximal portion to be connected to the screw thread 15 of inflow (venous) tube 16 (see FIG. 5). This temporarily secures the stiffening rod within the catheter 10 during insertion. External thread 85 is configured for threaded attachment of a syringe (not shown) for fluid flushing of the stiffener 80 (through lumen 81) prior to use. An example of a stiffening rod that also can be utilized is described in U.S. Pat. No. 7,077,829, the entire contents of which are incorporated herein by reference.

After the catheter 10 is positioned at the desired site, the stiffening member 80 is unthreaded from the proximal thread 15 of venous (return) tube 16 and removed from the venous lumen 50 of the catheter 10 and from the venous (return) tube 16.

It should be appreciated that the stiffening member 80 can alternatively be temporarily (removably) attached at its proximal end to the tube 16 by other means such as a bayonet lock, snap fit, etc. The stiffening member could first be manually twisted and then mounted by these various means for retention in its torqued position.

A dilator 90, illustrated in FIG. 6, can also be utilized during the insertion method. The dilator has a lumen 92 extending therethrough which receives the guidewire, e.g. guidewire 20. That is, the guidewire is threaded through the distal opening 93 in the distal end 91 of the dilator 90 and exits through proximal opening 95 at proximal end 97. The dilator 90 dissects tissue as it is advanced into the vessel over the guidewire. A tapered distal region helps to achieve such dissection. The proximal end 97 of dilator 90 has an external thread 99 to threadingly receive a syringe for flushing the dilator 90 with fluid through lumen 92 prior to use. Longitudinally extending raised surfaces 98 at the proximal end facilitate gripping of the dilator.

Tissue tunneling trocar device 100, shown in FIG. 7, has a proximal portion 102 and a distal portion 104. The trocar 100 can be in the form of a solid member. Proximal end 105 frictionally fits within the open distal end of the catheter, and particularly in the opening in the venous lumen 40. Bumps 106, 108, on the outer wall of the trocar 100 enhance the frictional engagement. The distal portion 104 has a curved region, terminating into an atraumatic tip 109 to bluntly dissect tissue as the catheter is inserted through the tissue tunnel. In use, bumps 106, 108 are inserted into the venous lumen 40 of the catheter, frictionally connecting the tunneling trocar 100 to the catheter 10. With the trocar 100 attached, the catheter 10 is inserted through the subcutaneous tissue tunnel with the tip 109 bluntly dissecting tissue. After the catheter emerges from the tissue tunnel, the trocar 100 is removed. A stiffener can then be inserted through the venous lumen 40 of the catheter as described above to receive the guidewire as described above.

A venous extension tube 16 and two arterial extension tubes 18a, 18b extend through the hub 12 to communicate with the lumens of the catheter tube 11 as shown in FIGS. 3 and 5. Tubes 18a, 18b are stacked in a vertical relationship. A venous clamp 27 is shown positioned over the venous tube 16 and an arterial clamp 29 is shown positioned over the two stacked arterial tubes 18a, 18b to cut off blood flow through both tubes 18a, 18b, preferably substantially simultaneously. An arterial tag 29a and venous tag 27a, to provide indication of priming volume or other information, are shown attached to the respective arterial and venous clamps. Additional details of the clamps and tags, e.g. the clamp posts to limit lateral movement of the stacked arterial extension tubes, are disclosed in U.S. Patent Publication 2008-0312578, the entire contents of which are incorporated herein by reference.

The catheter can optionally include a surface treatment on the exterior and/or the interior. The surface treatments can include for example, a hydrophilic coating to increase lubricity and facilitate insertion, a drug coating such as heparin or containing IIb, IIIa inhibitors, inert coating substances such as Sorins carbon coating, and/or active coatings such as a silver ion coating.

One method of insertion of the catheter of the present invention provides an entire over the wire system. This is achieved by the provision of a trocar such as disclosed in U.S.

Patent Publication 2008-0312578, the entire contents of which are incorporated herein by reference. The trocar has a lumen formed therethrough dimensioned for reception of a guidewire. The blunt distal tip of the trocar bluntly dissects tissue to create a subcutaneous tissue tunnel for subsequent securement of the catheter.

In use in a complete over the wire insertion method, first a needle is inserted into the internal jugular vein to properly locate the vessel and a guidewire is inserted through the needle into the right internal jugular vein "a" and into the superior vena cava "b". The guidewire is further advanced into the right atrium "c", and preferably into the inferior vena cava. The needle is then withdrawn, leaving the guidewire in place, extending out of the patient's body at the proximal portion. A dilator such as dilator 90 of FIG. 6 can be inserted over the guidewire to dilate tissue. Next, a trocar is inserted through a first incision in the patient, bluntly dissecting and tunneling under the skin, and forced out of the tissue at a second incision or site, creating a subcutaneous tunnel "t" under the tissue. This provides a way to secure the catheter. The guidewire is then threaded through the trocar lumen, with the proximal portion first inserted through trocar distal opening so it emerges out of a proximal opening. The trocar is then withdrawn from the body, leaving the guidewire in place, extending from the right atrium and superior vena cava, out through the right internal jugular vein and through the tissue tunnel "t".

Catheter 10 is then threaded over the guidewire with the proximal portion of the guidewire inserted through the distal tip lumen of the catheter, e.g. distal opening 49, through the length of the venous lumen 40, and through the hub 12 into the inflow tube 16. The catheter 10 is thus threaded over the wire, through the tissue tunnel "t" where a cuff is positioned in the tissue tunnel "t" to aid in securement of the catheter by enabling tissue ingrowth over a period of time. The catheter is further advanced over the guidewire down into the right internal jugular vein, into the superior vena cava, and into the right atrium "c". The guidewire 20 is then withdrawn, leaving the catheter 10 in place for use. Note a stiffening member such as stiffener 80 of FIG. 8, is preferably utilized, i.e. inserted into lumen 40 of catheter 10 and inserted over the guidewire through the fitting 15, inflow tube 16, and hub 12 to help guide the catheter as described herein. Thus, the guidewire would extend through the venous lumen of catheter by extending through the central lumen of the stiffening member which is positioned within the venous lumen 40 of the catheter.

As can be appreciated, the catheter will be inserted in a similar fashion through the left internal jugular vein. In this method, the subcutaneous tissue tunnel will be formed on the left side by the trocar, and the catheter inserted over the guidewire through the tissue tunnel and through the left internal jugular vein or subclavian vein and into the superior vena cava and right atrium in the same way as described for right side insertion In an alternative method of insertion, instead of forming a second incision site adjacent the incision site through which the needle and guidewire are introduced into the internal jugular vein, the trocar emerges from the needle/guidewire insertion site. In this method, the trocar is inserted through a first incision to create a subcutaneous tissue tunnel; however, unlike the aforementioned method, the trocar does not emerge at a second incision site. Instead, the trocar is advanced subcutaneously to the needle incision site and emerges through that site. Thus, the distal end of the trocar exits the incision site alongside the guidewire. The guidewire is then inserted (threaded) through the opening in the trocar as described above and then the trocar is withdrawn through the tissue tunnel 't' and out through the first incision such that the guidewire extends through the tunnel. After the guidewire 20 exits the tunnel "t" and out through the first incision, the trocar is removed, leaving the guidewire 20 in place. The guidewire is positioned to form a guidewire loop to facilitate insertion of the catheter.

The catheter 10 is then advanced over the guidewire and through the tissue tunnel and exiting the needle incision site into the internal jugular vein "a", tracking the loop of the guidewire, and then advanced downwardly through the internal jugular vein, the superior vena cava and into the right atrium "c". The guidewire is then withdrawn and the catheter is pushed downwardly and/or pulled back to straighten the loop. If the catheter is inserted with a stiffening member, the guidewire would extend through the lumen of the stiffening member as the stiffening member is positioned in the lumen of the catheter.

It should be appreciated that formation of the loop in the guidewire and the catheter is optional and the procedure can be performed without the loop.

In an alternative approach, a trocar is provided which does not provide for an entire over the wire system, however, it is used with an approach providing a partial over the wire system which eliminates the need for a tear way introducer sheath which often times is utilized to guide the dialysis catheter through the vessels into the right atrium. To avoid the use of the tear away sheath, the catheter in this alternate method can be advanced over a guidewire which can be placed in the manner described above. In this method, the trocar such as trocar 100 of FIG. 7, is attached to the distal end of the catheter by insertion of a barbed end into a mating fitting, or by other ways to temporarily attach the trocar. The trocar has a blunt distal tip and is advanced through a first tissue incision and out through a second tissue incision, bluntly dissecting tissue and forming a subcutaneous tissue tunnel in a similar manner as described above, except without the guidewire. Since the trocar is attached to the catheter, it pulls the catheter through the tissue tunnel, so it emerges out through the second incision. The trocar is then detached from the catheter. The catheter is then bent as necessary and threaded over the guidewire into jugular vein, superior vena cava, and right atrium.

In another method, a curved needle is used to create access to the site. A wire is passed through the needle to the site, the needle is then removed, and a dilator, such as dilator 90 of FIG. 6, is inserted over the wire. After dilating the tissue, the dilator is removed and the catheter 10 with a stiffening member positioned therein, such as stiffening member 80 of FIG. 8, are inserted over the guidewire into the right atrium.

It should be appreciated that although the catheter is described herein as a dialysis catheter for hemodialysis, the catheter disclosed herein could have other surgical applications, such as drug delivery or blood sampling.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A dialysis catheter for delivering and withdrawing blood from a patient's body, the dialysis catheter comprising a dialysis catheter body defining first, second, third and fourth quadrants in a transverse cross-section at an intermediate portion and having first and second arterial lumens and a venous lumen, the venous lumen positioned in a portion of the third and fourth quadrants with a first region adjacent the intersection of the four quadrants and a second region opposite the first region, a wall thickness of the dialysis catheter at the second region of the venous lumen having a first dimension and increasing in thickness in a direction toward the third quadrant and increasing in thickness in a direction toward the fourth quadrant to form a first arch shaped wall portion, the arch shaped wall portion thereby having a thinner portion at the portion aligned with a diameter bisecting the first and fourth quadrants from the second and third quadrants and progressively thicker portions in the third and fourth quadrants, and the first arterial lumen is positioned in a portion of the second and third quadrants and the second arterial lumen is positioned in a portion of the first and fourth quadrants, a major portion of the first arterial lumen and the center of the first arterial lumen being positioned in the second quadrant and a major portion of the second arterial lumen and the center of the second arterial lumen being positioned in the first quadrant, a dialysis catheter wall portion forming a second arch shaped wall portion adjacent the first arterial lumen, the second arch shaped wall portion having a first pinnacle in the second quadrant and the first pinnacle such that the first portion extends from the second quadrant into the third quadrant and the second portion extends within the second quadrant.

2. The dialysis catheter of claim 1, wherein dialysis catheter wall portion forms a third arch shaped wall portion adjacent the second arterial lumen, the third arch shaped wall portion having a second pinnacle and third and fourth portions of increasing thickness extending away from the second pinnacle such that the third portion of the third arch shaped wall portion extends from the first quadrant into the fourth quadrant and the fourth portion of the third arch shaped wall portion extends within the first quadrant.

3. The dialysis catheter of claim 1, wherein the first pinnacle of the second arch shaped wall portion lies in the second quadrant and the second pinnacle of third arch lies in the first quadrant.

4. The dialysis catheter of claim 1, wherein the venous lumen has a substantially circular cross-section positioned off center from a longitudinal axis of the catheter body.

5. The dialysis catheter of claim 3, further comprising a stiffening member removably positionable within the venous lumen of dialysis catheter to temporarily increase stiffness of the dialysis catheter to facilitate insertion.

6. The dialysis catheter of claim 2, wherein the venous lumen has a substantially circular cross-section positioned off center from a longitudinal axis of the dialysis catheter body.

7. The dialysis catheter of claim 1, wherein the first and second arterial lumens each contain walls of varying radius of curvature.

* * * * *